(12) United States Patent
Lehmann et al.

(10) Patent No.: US 9,205,121 B2
(45) Date of Patent: Dec. 8, 2015

(54) ECHINACEA FORMULATION (75) Inventors: Reg Lehmann, Bellbowrie (AU); Kerry Bone, Warwick (AU); Kerry Penman, St. Lucia (AU); Anita Matthias, Gordon Park (AU)

(73) Assignee: Integria Healthcare (Australia) PTY LTD, Eight Mile Plains (AU)

( * ) Notice: Subject to any disclaimer, the term of this patent is extended or adjusted under 35 U.S.C. 154(b) by 1367 days.

(21) Appl. No.: 12/882,723

(22) Filed: Sep. 15, 2010

(65) Prior Publication Data

US 2011/0059194 A1 Mar. 10, 2011

Related U.S. Application Data (63) Continuation of application No. 11/631,902, filed as application No. PCT/AU2005/000993 on Jul. 6, 2005, now abandoned.

(30) Foreign Application Priority Data

Jul. 7, 2004 (AU) ............................... 2004903716

(51) Int. Cl.
*A61K 36/28* (2006.01)
(52) U.S. Cl.
CPC ..................................... *A61K 36/28* (2013.01)
(58) Field of Classification Search
None
See application file for complete search history.

(56) References Cited

U.S. PATENT DOCUMENTS

| | | | |
|---|---|---|---|
| 4,313,930 A | 2/1982 | Wischniewski et al. | |
| 4,857,512 A * | 8/1989 | Wagner et al. .................. | 514/54 |
| 5,578,307 A | 11/1996 | Wunderlich et al. | |
| 6,224,871 B1 * | 5/2001 | Hastings et al. ......... | 424/195.17 |
| 6,306,443 B1 | 10/2001 | Brovelli et al. | |
| 7,071,233 B2 | 7/2006 | Squires | |
| 2002/0146473 A1 | 10/2002 | Menon et al. | |
| 2003/0152653 A1 | 8/2003 | Gahler et al. | |
| 2005/0175721 A1 | 8/2005 | Brovelli et al. | |

FOREIGN PATENT DOCUMENTS

| | | |
|---|---|---|
| CH | 676931 A5 | 3/1991 |
| EP | 0464298 | 1/1992 |
| EP | 0722719 A1 | 7/1996 |
| EP | 0770394 A2 | 5/1997 |
| EP | 1220680 A2 | 7/2002 |
| JP | 2000026317 A | 1/2000 |
| WO | 98/11778 A1 | 3/1998 |
| WO | 0006188 A1 | 2/2000 |
| WO | 01/22977 | 4/2001 |
| WO | 01/54673 A1 | 8/2001 |

OTHER PUBLICATIONS

Franci, et al. Levels of Active Constituents in Manufactured Exhinacea Products, Chemistry in Australia, Sep. 1998, p. 17-19.
A. Matthias, Permeability Studies of Alkylamides and Caffeic Acid Conjugates From Echinacea Using a Caco-2 Cell Monolayer Model, Journal of Clinical Pharmacy and Therapeutics 29, pp. 7-13 (Feb. 30, 2004).
Wills Fraci et al., Levels of Active Constituents in Manufactured Echinacea Products. Chemistry in Australia, Sep. 17-19, 1998, Department of Food Technology.
R.R. Buresh, Notification of Statements of Nutritional Support, Centre for Food Safety and Applies Nutrition, Food and Drug Administration, 1998.
Bruce Barrett et al, Treatment of the Common Cold With Unrefined Echinacea: A Randomised Double Blind, Placebo-Controlled Trial, Annals of Internal Medicine 137, pp. 939-945, (12) 2002.
Pietta et al; MEKC Analysis of Different *Echinacea* Species. Planta Medica 64 (1998), pp. 649-652.
R. Bauer, Standardization of Echinacea Purpurea Expressed Juice With Reference to Cichoric Acid and Alkamides; Journal of Herbs, Spices & Medicinal Plants, vol. 6(3)1999, pp. 51-62.
Barbara Muller-Jakic et al, In Vitro and Inhibition of Cyclooxygenase and 5-Lipdxygenase by Alkylamides From *Echinacea* and *Achillea* Species; Planta Medica; 60(1994), pp. 37-40.
H. Jager et al, Transport of Alkamides From *Echinacea* Species Through Caco-2 Monolayers; Planta Medica 2002; 68, pp. 469-471.
Nigel Perry et al, Alkamide Levels in Echinacea Purpurea; Effects of Processing, Drying and Storage; Planta Medica 66 (2000), pp. 54-56.
Birgit Dietz et al, Absorption of Dodeca-2E, 4E, 8Z, 10E/Z-Tetraenoic Acid Isobutylamides After Oral Application of Echinacea Purpurea Tincture; Planta Med 67 (2001), pp. 863-864.
Xian-guo He et al, Analysis of Alkamides in Roots and Achenes of Echinacea Purpurea by Liquid Chromatography-Electrospray Mass Spectrometry, Journal of Chromatography A 815 (1998), pp. 205-211.
Nigel Perry, et al, Alkamide Levels in Echinacea Purpurea; A Rapid Analytical Method Revealing Differences Among Roots, Rhizomes, Stems, Leaves and Flowers, Planta Medica 63 (1997), pp. 58-62.
R. Bauer et al, New Alkamides From Echinacea Angustifolia and E. Purpurea Roots, Planta Medica 1988, pp. 563-564.
Wu et al, 2004 Phytochemistry, 65, pp. 2477-2484.
WHO Monographs on Selected Medicinal Plants—vol. 1 (1999) 295.
Assessment of the Pharmacology, Toxicology, Safety and Efficacy of *Echinacea* Species, Jun. 9, 2000.
Awang, D.V.C. 1999, Immune Stimulants and Antiviral Botanicals: Echinacea and Ginseng. pp. 450-456, In: J Janick (ed), Perspectives on new crops and new uses, ASHS Press, Alexandria, VA.
International Search Report dated May 23, 2001, corresponding to PCT/CA01/00106.
Chemical Abstracts, vol. 132, No. 9, Feb. 8, 2000 (Feb. 28, 2000) Columbus, Ohio, US; abstract No. 113087.

(Continued)

*Primary Examiner* — Terry A McKelvey
*Assistant Examiner* — Catheryne Chen
(74) *Attorney, Agent, or Firm* — Locke Lord LLP; Jeffrey D. Hsi; Gabriel J. McCool (57) ABSTRACT

The present invention relates to an *Echinacea* formulation which includes an alkylamide fraction comprising a 2-ene alkylamide fraction and a 2,4-diene alkylamide fraction and the weight ratio of the 2-ene alkylamide fraction to the 2,4-diene alkylamide fraction is between about 1:15 to about 2:1.

12 Claims, 7 Drawing Sheets

(56) References Cited

OTHER PUBLICATIONS

Matthias, et al., "Cytochrome P450 Enzyme-Mediated Degradation of Echinacea Alkylamides in Human Liver Microsomes", Chemico-Biological Interactions, (2005), 155, 62-70.

Gilroy, Christine, et al., "Echinacea and Truth in Labeling," Arch Intern Med, vol. 163, Mar. 24, 2003, 699-704.

Willis, et al., "Alkylamide and Cichoric Acid Levels in Echinacea Purpurea Grown in Australia", Food Chemistry 67 (1999) 385-388.

Industry Report: Guidance for industry: Substantiation for dietary supplement claims made under section 403(r)(6) of the Federal Food, Drug and Cosmetic Act, The United States of America, Department of Health and Human Services, Food and Drug Administration, Jan. 10, 2005.

Karen Gunning, Echinacea in the Treatment and Prevention of Upper Respiratory Tract Infections WJM Sep. 1999 (171).

\* cited by examiner

ECHINACEA FORMULATION

This application is a continuation of U.S. patent application Ser. No. 11/631,902, filed Nov. 29, 2007, which is a 371 national phase entry of PCT/AU05/00993, which was filed on Jul. 6, 2005, both of which are incorporated herein by reference in their entirety.

FIELD OF THE INVENTION

The present invention relates to an *Echinacea* formulation for oral administration.

BACKGROUND OF THE INVENTION

*Echinacea* is a herb well known for its immune stimulatory activity. *Echinacea* formulations are widely available to the public and are commonly taken for the prevention and treatment of colds and flu.

Traditionally, herbal medicines were available in liquid form as tinctures, teas and the like. However, liquids are not favored by the public for reasons such as taste and convenience. Thus, herbal preparations are generally commercially available in tablet or capsule form. Many tablets are comprised simply of ground dried herb. A disadvantage of ground herbal products is that they contain large amounts of inert plant matter as compared to the active components. Thus relatively large numbers of relatively large tablets need to be consumed for a patient to obtain a therapeutic dose of active ingredients. This may meet with consumer resistance and lead to non-compliance. As such, formulations are generally classified simply by weight of the source herb, the actual content of purported active is not only unknown but can vary significantly from batch to batch.

Other preparations are available in the form of concentrated extracts which are obtained by hydroalcoholic extraction of the herb. An advantage of the concentrated extract is that the soluble constituents of the herb, including the actives, are separated from the inert plant material, thereby decreasing the total volume of material which must be ingested to obtain a therapeutic dose. Concentrated extracts are often standardized to a concentration of a marker compound. Herbal extracts are ideally standardized with respect to the level of an active ingredient such that the effects of batch to batch variations may at least partially be negated, whilst providing an indication as to potency of a particular dosage unit. Difficulties arise however, where the identity of the active compounds are unknown or uncertain. Many manufacturers of *Echinacea* formulations produce extracts standardized to echinacoside or cichoric acid.

There are many hundreds of commercial preparations identified by the term *Echinacea*, the content and chemical profile of which preparations vary significantly. There are a number of reasons for such variance. First, there are three species of *Echinacea*, which are used commercially; *E. purpurea, E. angustifolia* and *E. paffida*. Different species contain different levels of active agents and commercial preparations may be sourced from any one or more of these species. Further, different parts of the plant contain different levels of active agents and various parts of the plant such as the root or the aerial parts (leaf, flower or stem) may be and are used as a source of *Echinacea* preparations. Commercial preparations are commonly sourced from the juice obtained from the aerial parts of *E. purpurea*. *E. purpurea* has been favoured due to its ease of cultivation and lower cost. Other preparations are sourced from fresh or dried whole plant, aerial parts or root of one or more of the above three species, hydroalcoholic extracts, or mixtures of any of these.

The literature is replete with reports of studies which have been conducted in an effort to learn more about the action of *Echinacea* and also to test the efficacy of various preparations. Despite the amount of available literature on the subject, it is still not clear from the available evidence as to which constituents or combinations thereof are responsible for the pharmacological activity of *Echinacea*. Many in vivo studies are in conflict and inconclusive. Some trials concluded that *Echinacea* was effective in treating the common cold, whereas other studies could draw no such conclusion. In many cases, trials were conducted on samples which were poorly, if at all, quantified with respect to potentially active components. Thus it is difficult to draw any meaningful conclusions from such trials. In other cases conclusions as to in vivo activity have been drawn from in vitro studies without due consideration being given to the inherent difficulties associated with such extrapolation.

The constituents of *Echinacea* which have received the most attention are the caffeic acid derivatives such as echinacoside and cichoric acid, polysaccharides and alkylamides (also called alkamides). Echinacoside has been reported to have antibacterial and antiviral activity. However, there is no evidence to date that supports any immunomodulatory activity. On the other hand, cichoric acid has been observed to cause a marked stimulation of phagocytosis in vitro and in vivo. This suggests cichoric acid may be an important contributor to the therapeutic effect of *Echinacea*. However, the present inventors have observed that cichoric acid and echinacoside exhibit very poor passage across Caco-2 cell monolayers. Such monolayers are used to model the absorption of compounds across the intestinal barrier. The present inventors have therefore suggested that caffeic acid conjugates such as cichoric acid and echinacoside, due to poor permeability across the is intestinal barrier, may not be responsible for the observed in vivo effects of *Echinacea*.

In vitro research has also suggested that the polysaccharides promote T cell activity and many commercial *Echinacea* products are promoted on this basis. However, the relationship between this in vitro work and the therapeutic effects of *Echinacea* have been questioned for a number of reasons. For example, research has shown that absorption in the gut of similar polysaccharides found in Aloe Vera juice is about 1%. This suggests that insufficient levels of polysaccharides from *Echinacea* would be absorbed to have any biological effect. Further as polysaccharides are sparingly soluble in ethanol, it is believed that negligible quantities of polysaccharides would be present in hydroalcoholic extracts. However, in vivo studies have shown that such hydroalcoholic extracts do indeed exhibit an immunomodulating effect.

The alkylamides are found in *E. angustifolia* and *E. purpurea* but are largely absent from *E. pallida*. These alkylamides are unsaturated butylamides and may be classified into two groups, the 2-ene and 2,4-diene alkylamides. These alkylamides may be represented by the following formulae:

-continued wherein $R^1$ is H or Me; $R^2$ is a $C_6$ to $C_{10}$ saturated or unsaturated carbon chain and $R^3$ is a $C_5$ to $C_9$ saturated or unsaturated carbon chain.

The ratio of these two classes of alkylamides may vary considerably depending upon the source. Both root and aerial parts of *E. purpurea* contain low levels of the 2-enes whereas *E. angustifolia* root contains a relatively large proportion of the 2-enes.

In view of the significance of *Echinacea* as both a commercial and therapeutic product, many manufacturers of herbal medicines have sought to develop products which they can claim to have superior efficacy or potency over a competitor's product. Some manufactures have sought to formulate synergistic combinations of *Echinacea* with other extracts such as *Panax Ginseng*, Goldenseal or Cat's Claw. Other preparations combine an *Echinacea* extract with vitamins and minerals which are believed to assist in is the treatment of colds and flu. Combining an *Echinacea* extract with agents known to increase the biological effectiveness of biologically active agents has also been proposed. Such agents include the salts of succinic acid.

Another approach with a view to improving commercially available products has been to provide different methods of formulation. As mentioned above herbal medicines were traditionally available as liquids. It is generally believed that a liquid system is a more efficient delivery system than a solid system for reasons of dissolution and solubility. However, as also mentioned earlier, there is consumer resistance to such delivery methods. Thus there have been attempts to formulate an *Echinacea* product in capsule form which may have improved solubility and absorption properties. To this end microencapsulated *Echinacea* formulations have appeared in the market place. Microencapsulation is well known in the pharmaceutical arts to increase the solubility of an active compound and involves encapsulating droplets of liquids by a thin coating.

In the light of the current information and understanding of those in the art regarding *Echinacea*, the present inventors have undertaken studies to investigate those compounds in *Echinacea* which not only exhibit an immunomodulatory effect but are also bioavailable. For example, one such study investigated the effect of *Echinacea* intake in human subjects on the immune response through altered expression of heat shock protein (hsp70) in leucocytes, increased white blood cell counts and improved erythrocyte antioxidant defenses. The *Echinacea* was a tablet form of a ethanolic extract of the root of *E. purpurea* and *E. angustifolia*. The results after a two week dosing regime showed that *Echinacea* affected the immune system by increasing white cell counts and the response of hsp70 in leucocytes to heat shock as well as decreasing erythrocyte haemolysis. The inventors also identified the presence of an alkylamide in the blood of all subjects, strongly suggesting that the alkylamide was responsible for the observed effects. The presence of the alkylamide was inconsistent with earlier observations that the alkylamides in solid *E. purpurea* preparations are rapidly metabolized in the liver and are poorly bioavailable.

In another study in which the present inventors participated, the is modulation of macrophage immune response by an ethanolic extract of *E. purpurea* and *E. angustifolia* roots was investigated.

Macrophages play an essential role in the development of specific and non-specific immune responses. Upon activation by a variety of stimuli macrophages release a number of products having biological activity. Such products include cytokines, such as TNF-α, NF-κB and nitric oxide (NO). Macrophages undergo a process of cellular "activation" which is associated with morphological, functional, and biochemical changes in the cells in response to inflammatory signals or antigens. One prominent characteristic of activated macrophages is their increased capacity to release pro-inflammatory and cytotoxic mediators, which help aid in the resolution of infection or inflammation. As a prelude to macrophage activation LPS must bind to a receptor on the macrophage cell surface. Several LPS receptors have been identified in different macrophages with the most thoroughly studied receptor being the CD14 receptor. The mouse peritoneal macrophage cell line, RAW 264.7 used in this study possesses the CD14 receptor.

Figure 1:
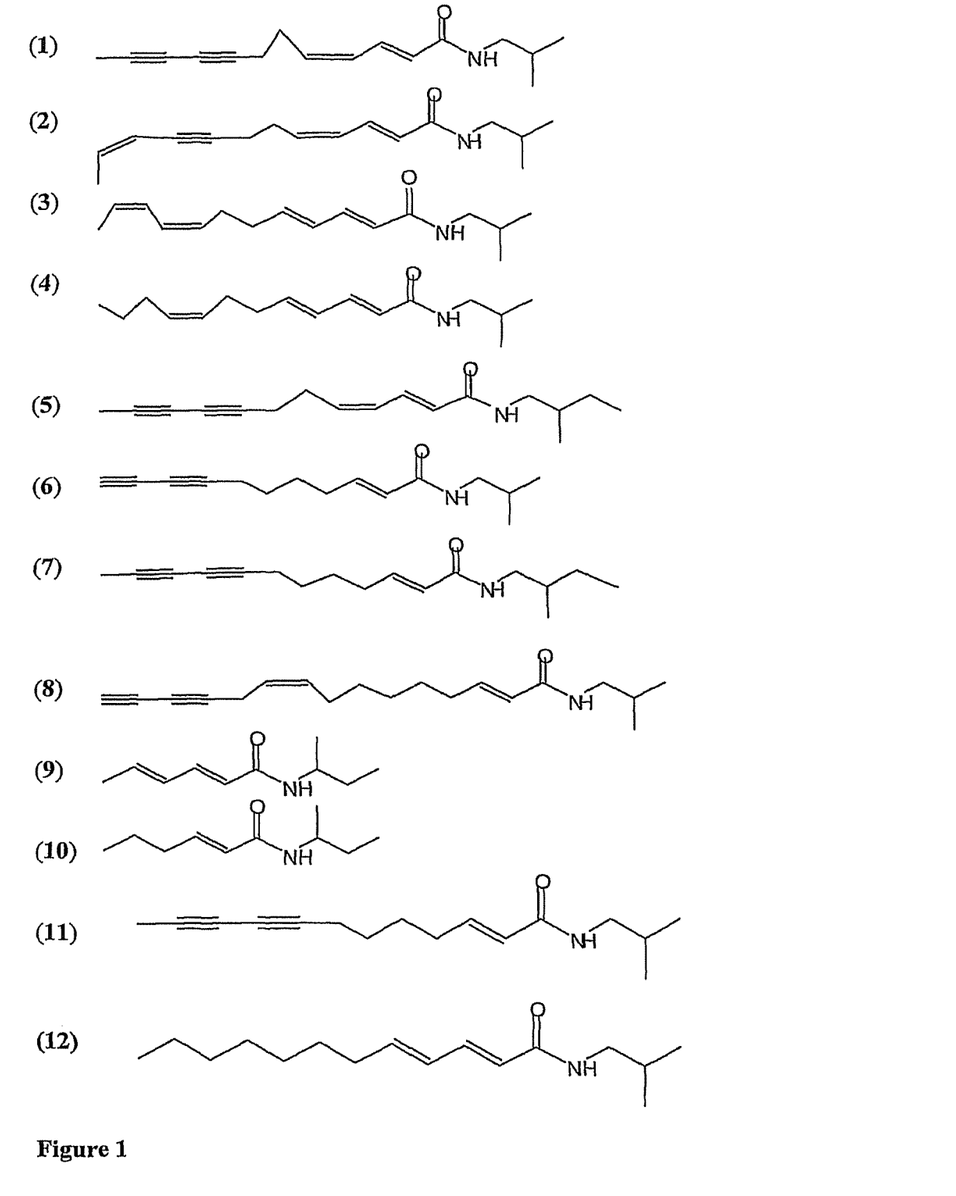
FIG. 1 shows structures of isobutylamides and methylbutylamides.

In this study, the activity of an ethanolic *Echinacea* extract containing both caffeic acid conjugates and alkylamides on NF-κB, TNF-α and NO were compared to that of the alkylamide fraction alone, cichoric acid and a synthetic 2-ene alkylamide and a synthetic 2,4-diene alkylamide. The synthetic alkylamides correspond to the major 2-ene and 2,4-diene alkylamides found in *Echinacea*. These alkylamides are illustrated in FIG. 1 as compounds 6 and 3 respectively.

The results showed that all components tested except the 2-ene alkylamide significantly decreased lipopolysaccharide (LPS) stimulated NF-κB levels. Only cichoric, the *Echinacea* extract and the alkylamide mixture significantly decreased TNF-α production under LPS stimulated conditions in macrophages. Only the alkylamide mixture decreased LPS stimulated NO production. The mixture of alkylamides in the *Echinacea* ethanolic liquid extract did not respond in the same manner in the assays as the individual alkylamides investigated.

These results demonstrate that the alkylamides, cichoric acid and *Echinacea* are an effective modulator of macrophage immune responses in vitro. However, it is believed that it is unlikely that cichoric acid would have any observable effect in vivo in view of it's low permeability across Caco-2 monolayers.

The present invention relates to the surprising and unexpected discovery by the inventors that the 2-ene alkylamides are metabolized by the liver at much lower rates that the 2,4 diene alkylamides and still further that the 2-ene alkylamides can actually inhibit 2,4-diene liver metabolism.

DESCRIPTION OF THE INVENTION

According to a first broad form of the invention there is provided an *Echinacea* formulation which includes an alkylamide fraction comprising a 2-ene alkylamide fraction and a 2,4-diene alkylamide fraction and the weight ratio of the 2-ene alkylamide fraction to the 2,4-diene alkylamide fraction is between about 1:15 to about 2:1.

The ratio of the 2-ene alkylamide fraction to the 2,4-diene alkylamide fraction is preferably between about 1:10 to about 2:1, most preferably between about 1:9 to about 1:1. Especially preferred is a ratio between about 1:8 to about 1:5.

The formulation may be in any form suitable for oral administration. Such forms are well known in the art and include liquids, tablets, capsules, powders and the like. Typically, the formulation is in the form of a solid unit dose.

Generally the formulation includes an extract of *E. angustifolia* root as a source of the 2-ene alkylamide fraction. Typically, the formulation includes a dried hydroalcoholic extract of *E. angustifolia* root, although ground herb could also be used. The extract may be obtained by any suitable method which will at least partially extract the 2-ene alkylamides contained therein. The *E. angustifolia* extract may be in the form of an alkylamide enriched extract.

*E. angustifolia* root contains a number of 2-ene alkylamides, of which (2E)-N-isobutylundeca-2-ene-8,10-diynamide is generally the most common. Thus a typical formulation of the invention may include a 2-ene alkylamide fraction containing (2E)-N-isobutylundeca-2-ene-8,10-diynamide and at least is one or more further 2-ene alkylamides. It is preferred that (2E)-N-isobutylundeca-2-ene-8,10-diynamide is the major 2-ene alkylamide in the 2-ene alkylamide fraction of the formulation of the invention. Typically, the 2-ene alkylamide fraction includes at least 30 wt % (2E)-N-isobutylundeca-2-ene-8,10-diynamide. It will be appreciated that (2E)-N-isobutylundeca-2-ene-8,10-diynamide may also be the sole or essentially the sole 2-ene alkylamide in the 2-ene alkylamide fraction.

Other 2-ene alkylamides which may be present in an *E. angustifolia* extract include, but are not limited to, (2E)-N-(2-methylbutyl)dodeca-2-ene-8,10-diynamide, (2E,7Z)—N-isobutyltetradeca-2,7-diene-10,12-diyamide, (2E,9Z)—N-isobutylpentadeca-2,9-12,14-diynamide and (2E,9Z)—N-(2-methylbutyl)pentadeca-2,9-diene-12,14-diynamide.

The 2,4-diene alkylamides may be found in the aerial parts and roots of both *E. purpurea* and *E. angustifolia*. Preferably both plants are used as a source of the 2,4-diene alkylamides. Although the 2,4-diene alkylamides are found in root and aerial parts of these species, it is preferred that the alkylamides are sourced from the root of each plant. These plants typically contain a number of 2,4-dienes, of which (2E,4E,8Z,10Z)—N-isobutyldodeca-2,4,8,10-tetraenamide is generally the most common. Thus a typical formulation of the invention may include a 2,4-diene alkylamide fraction containing (2E,4E,8Z,10Z)—N-isobutyldodeca-2,4,8,10-tetraenamide and at least one or more further 2,4-diene alkylamide. It is preferred that (2E,4E,8Z,10Z)—N-isobutyldodeca-2,4,8,10-tetraenamide is the major 2,4-diene alkylamide in the 2,4-diene alkylamide fraction of the formulation of the invention. Typically, the 2,4-diene alkylamide fraction includes at least 30 wt % (2E,4E,8Z,10Z)—N-isobutyldodeca-2,4,8,10-tetraenamide.

Other 2,4-diene alkylamides which may be present in the 2,4-diene alkylamide fraction include, but are not limited to, are (2E,4Z)—N-isobutylundeca-2,4-diene-8,10-diynamide, (2E,4Z)—N-isobutyldodeca-2,4-diene-8,10-diynamide, (2E,4Z,8Z)—N-isobutyldodeca-2,4,10-triene-8-ynamide, (2E,4E,8Z,10E)-N-isobutyldodeca-2,4,8,10-tetraenamide, (2E,4E,8Z)—N-isobutyldodea-2,4,8-trienamide, (2E,4E)-N-isobutyldodeca-2,4-dienamide and (2E,4Z)—N-(2-methylbutyl)dodeca-2,4-diene-8,10-diynamide.

Typically, a formulation of the present invention will include both (2E)-N-isobutylundeca-2-ene-8,10-diynamide and (2E,4E,8Z,10Z)—N-isobutyldodeca-2,4,8,10-tetraenamide. Typically, there alkylamides are in a weight ratio of between about 1:10 to about 1:1, preferably between about 1:6 to about 1:2, most preferably between about 1:4.5 to about 1:2.5.

The relative amounts of 2-ene and 2,4-diene alkylamides in *E. angustifolia* root may vary depending upon the age of the plant, flower developmental stages and growing, harvesting and storage conditions. Further, extraction parameters such as solvent, temperature and length of extraction period will also affect the total and relative alkylamide levels in any extract. Accordingly, the amounts of *E. angustifolia* extract required to be included with a formulation containing a mixture of *E. angustifolia* and *E. purpurea* may vary on a batch to batch basis. Thus in order to manufacture the formulation of the present invention it is desirable to measure the relative amounts of the 2-ene alkylamides and 2,4-diene alkylamides in the respective *Echinacea* extracts prior to admixture such that the relative amounts of *E. angustifolia* and *E. purpurea* may be adjusted to provide the desired ratio of alkylamides. The respective extracts may be analyzed for either the total 2-ene or 2,4-diene alkylamide content or alternatively the content of the generally most common alkylamides (2E)-N-isobutylundeca-2-ene-8,10-diynamide and (2E,4E,8Z,10Z)—N isobutyldodeca-2,4,8,10-tetraenamide.

According to a further broad form of the invention there is provided a method of preparing an *Echinacea* formulation, the method comprising providing an extract of *E. angustifolia* root and an extract of *E. purpurea*, analyzing the *E. angustifolia* extract for 2-ene alkylamides and/or (2E)-N-isobutylundeca-2-ene-8,10-diynamide content and both extracts for 2,4-diene alkylamides and/or (2E,4E,8Z,10Z)—N isobutyldodeca-2,4,8,10-tetraenamide content, and combining the two extracts such that the weight ratio of total 2-ene alkylamides total 2,4-diene alkylamides in the combined extract is between about 1:15 to about 2:1 or the weight ratio of (2E)-N-isobutylundeca-2-ene-8,10-diynamide to (2E,4E,8Z,10Z)—N isobutyldodeca-2,4,8,10-tetraenamide in the combined extract is between about 1:10 to about 1:1.

Alternatively the *E. angustifolia* extract and/or combined formulation is is standardized to 2-ene alkylamide and/or (2E)-N-isobutylundeca-2-ene-8,10-diynamide content.

According to a further form of the invention, there is provided an *Echinacea* formulation which includes an extract of *E. angustifolia* comprising a 2,4-diene alkylamide fraction and a standardized amount of a 2-ene alkylamide fraction, wherein the weight ratio of the 2-ene alkylamide fraction to the 2,4-diene alkylamide fraction is from about 1:15 to about 2:1.

The formulation may alternatively be standardized with respect to a specific 2-ene alkylamide. In the latter case, it is preferred that the formulation is standardized to (2E)-N-isobutylundeca-2-ene-8,10-diynamide. Typical standardized amounts of the whole 2-ene alkylamide fraction range from about 0.002 to about 2 w/w %, typically between about 0.02 to about 1 w/w %, preferably between about 0.04 to about 0.1 w/w %. Typical standardized amounts of (2E)-N-isobutylundeca-2-ene-8,10-diynamide range from about 0.001 to about 1 w/w %, typically between about 0.01 to about 0.5 w/w %, preferably between about 0.02 to about 0.05 w/w %.

According to a still further form of the invention, there is provided a method of preparing an *Echinacea* formulation, the method comprising combining *E. angustifolia* root, or an extract thereof and *E. purpurea* or an extract thereof and standardizing the combination to at least one 2-ene alkylamide.

The total level of alkylamides in the formulations of the invention is typically between about 0.01 to 10 w/w %, preferably between about 0.2 to about 3 w/w %.

It will be appreciated that the formulation may also include other herbs, or parts or extracts thereof and pharmaceutically acceptable, recipients, diluents, carriers and/or adjuvant.

The formulation may also include means for enhancing the solubility of the alkylamides. Such means are known in the art and include microencapsulation.

DESCRIPTION OF THE FIGURES

(1) (2E,4Z)—N-isobutyldodeca-2,4-diene-8,10-diynamide mw=243;
(2) (2E,4Z,10Z)—N-isobutyldodeca-2,4,10-triene-8-ynamide mw=245;
(3) (2E,4E,8Z,10Z)—N-isobutyldodeca-2,4,8,10-tetraenamide mw=247;
(4) (2E,4E,8Z)—N-isobutyldodeca-2,4,8-trienamide mw=249;
(5) (2E,4Z)—N-(2-methylbutyl)dodeca-2,4-diene-8,10-diynamide mw=257;
(6) (2E)-N-isobutylundeca-2-ene-8,10-diynamide mw=231;
(7) (2E)-N-(2-methylbutyl)dodeca-2-ene-8,10-diynamide mw=259;
(8) (2E,9Z)—N-isobutylpentadeca-2,9-diene-12,14-diynamide mw=285
(9) (2E,4E)-N-(sec-butyl)hexa-2,4-dienamide mw=167;
(10) (2E)-N-(sec-butyl)hex-2-enamide mw=169;
(11) (2E)-N-isobutyldodeca-2-ene-8,10-diynamide mw=245;
(12) (2E-4E)-N-isobutyldodea-2,4-dienamide mw=251.

EXAMPLES

Degradation of *Echinacea* Alkylamides in Human Liver Microsomes

This study was designed to investigate the metabolic stability of various alkylamides in vitro in the presence of sub cellular fractions of liver.
Chemicals
Alkylamides 3, 6, 11 and 12 were synthesised according to the method previously described [1] (see FIG. 1 for structures of the synthesised alkylamides). The *Echinacea* extract (EE) was an ethanolic extract of a mixture of *Echinacea angustifolia* (200 mg/mL) and *Echinacea purpurea* (300 mg/mL) roots extracted in 60% ethanol/water.

The EE alkylamide fraction was separated from the caffeic acid fraction by diluting 1:100 with water and fractionated on a solid phase extraction cartridge (Strata C18-E; 55 mm, 70 Å; 500 mg/6 mL; Phenomenex, USA) conditioned with 10 mL of 70% ethanol then 5 mL water. The caffeic acids were eluted from the column with water and 7% ethanol and then discarded. The alkylamide fraction was eluted using 70% ethanol and diluted back to a concentration equivalent to that found initially in the ethanolic extract.

Figure 2:
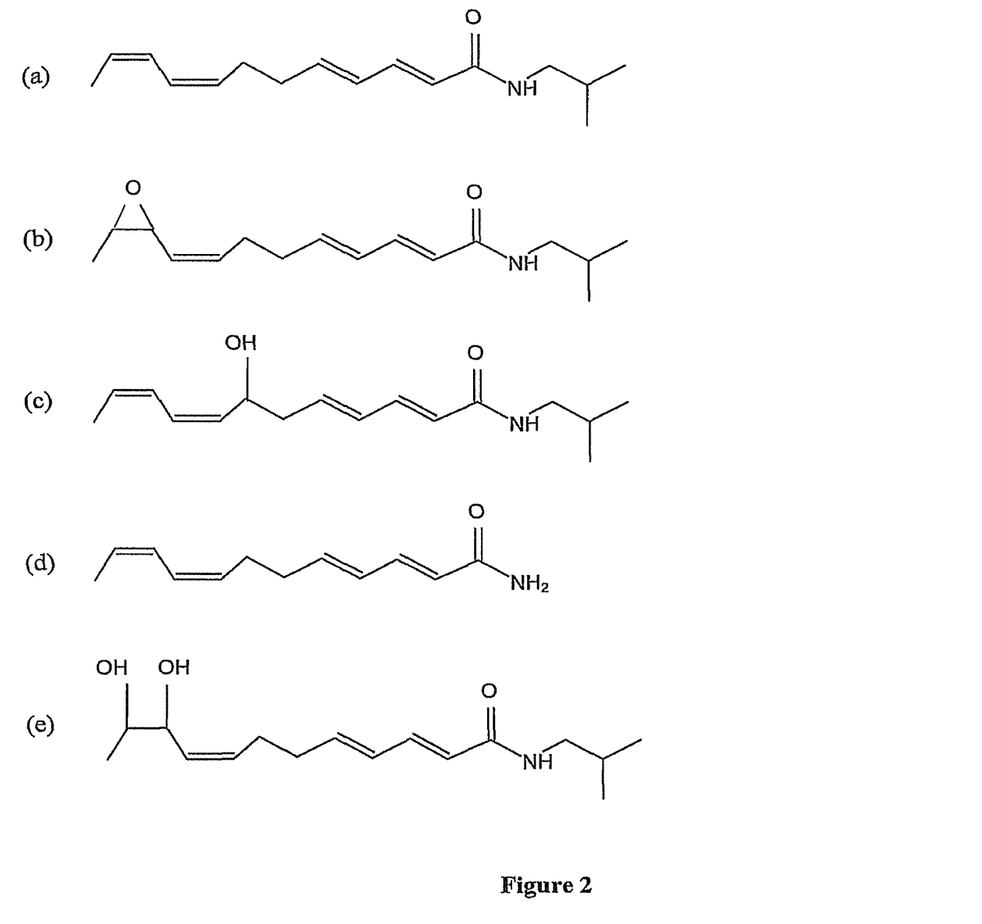
FIG. 2 shows representative structures of possible isobutylamide metabolites for (2E,4E,8Z,10Z)—N-isobutyldodeca-2,4,8,10-tetraenamide mw=247 (3). (a) Parent compound; (b) an example of the epoxidation of a double bond; (c) an example of hydroxylation at a saturated C; (d) dealkylated product resulting from hydroxylation at the methylene next to the amide N; (e) an example of a diol formed from further transformation of the initial epoxide metabolite as seen in (b)

Epoxides corresponding to oxidation of the 8,9 (structure not shown) and 10,11 (FIG. 2b) double bonds were synthesised as a 1:2 mixture respectively via a meta-chloroperbenzoic acid epoxidation of the alkylamide (2E,4E,8Z,10Z)—N-isobutyldodeca-2,4,8,10-tetraenamide (3). These two epoxides co-eluted using flash chromatography (silica gel) and the mix was isolated as a colourless oil. These two major products displayed spectral data consistent with epoxidation occurring at these two double bonds.

Data for the mixed epoxides are as follows: $^1$H NMR (500 MHz)/$C_6D_6$:d 0.86 (d, 6H, 6.69 Hz, ($\underline{H}_3C)_2CH$—), 1.13 (d, 2H, 5.43 Hz, $\underline{H}_3CCH(O)CH$), 1.61 (dd, 1H, 1.67 Hz, 9.15 Hz, $\underline{H}_3CCH=CH$—), 1.73 (m, 1H, $(CH_3)_2C\underline{H}CH_2$—), 1.96-2.22 (m, 4H, —CH=CHC$\underline{H}_2$—), 2.85-2.90 (m, 0.33H, —C$\underline{H}(O)CH(O)CH=$), 2.92-3.0 (m, 0.66H, —C$\underline{H}(O)CH(O)CH=$), 3.72 (t, 2H, 6.74 Hz, NHC$\underline{H}_2CH(CH_3)_2$), 3.43-3.48 (m, 0.66H, —CH(O)C$\underline{H}(O)CH=$), 3.52-3.58 (m, 0.33H, —CH(O)C$\underline{H}(O)CH=$), 5.28-5.37 (m, 1H, —CH=C$\underline{H}CH(O)CH(O)$—), 5.40-5.47 (m, 1H, —CONHC$\underline{H}_2$—), 5.54-5.71 (m, 1H, —C$\underline{H}$=CHCH(O)CH(O)—), 5.72 (d, 1H, 14.73 Hz, —CH=C$\underline{H}CONH$—), 5.79 (dt, 1H, 15.16 Hz, 6.94 Hz, —$CH_2C\underline{H}$=CH—CH=), 6.16 (m, 1H, —$CH_2CH$=C$\underline{H}$—CH=), 7.60 (m, 1H, —C$\underline{H}$=CHCONH). $^{13}$C NMR (125 MHz)/$C_6D_6$:d 13.29, 13.71, 20.09, 27.13, 27.88, 28.91, 29.94, 32.84, 46.93, 52.36, 52.44, 53.46, 57.18, 123.48, 123.50, 125.37, 125.48, 129.36, 129.41, 130.89, 135.32, 140.52, 140.58, 140.59, 165.51. GCMS m/z (E/I) 264 ($M^+$, 0.5), 263 (3), 248 (0.5), 220 (3), 197 (5), 180 (13), 166 (17), 152 (34), 135 (9), 110 (12), 107 (15), 94 (12), 81 (21), 79 (20), 67 (33), 66 (34), 57 (96), 43 (100).

Liver Microsomes and Recombinant P450s
Livers were obtained from organ donors according to procedures is approved by the University of Queensland ethics committees. Samples of human liver were frozen in liquid nitrogen and stored at −70° C. prior to use. Microsomes were prepared according to the method of Guengerich [2] except that microsomes were subjected to a final wash in 10 mM Tris-acetate, 1 mM EDTA and 20% glycerol pH 7.4 (resuspension buffer) to remove residual drugs (e.g. phenytoin—data not shown) present in donor livers.

Recombinant P450s were co-expressed with hNPR in *Escherichia coli* according to the general procedures outlined previously [8]. Recombinant P450 preparations were obtained from bacteria transformed with bicistronic expression vectors for P450s 1A1, 1A2, 2D6, 2E1 and 3A4 [6]; 1B1 [10]; 2A6 [8]; P450 2B6 [11]; 2C9 (wild type; P450 2C9*1) and 2C19 [12]; 3A5 and 3A7 [12] and 4A11 (D. Kim and F. P. Guengerich, unpublished data). cDNAs for P450s 2C8 and 2C18 were obtained from Prof D. J. Birkett (Flinders University of South Australia) and Prof. Philippe Beaune (INSERM U490, Universite Rene Descartes, Paris V, France) respectively, and bicistronic constructs in pCW were made according to previously published methods [3,4]. Membranes from cells transformed with the monocistronic expression vector for recombinant human reductase, pCW'/hNPR, were used as a negative control. Expression of P450s and preparation of bacterial membrane fractions was done according to established methods [5,6].

The P450 contents of bacterial membranes and liver microsomes were quantified by $Fe^{2+}$. CO versus $Fe^{2+}$ difference spectroscopy according to the general method of Omura and Sato [7]. NADPH-P450 reductase concentrations were quantified as described previously [8] using a specific activity of 3200 nmol cyt c reduced $min^{-1}$ nmol $hNPR^{-1}$ [16]. Protein concentrations were determined using the BCA method (Pierce, Rockford, Ill.) according to the manufacturer's instructions.

Enzyme Assays

Incubations (0.5 mL) with tissue fractions contained either the microsomal fraction at 0.1-0.2 mM P450 or the cytosolic fraction at 5 mg/mL protein in 100 mM potassium phosphate (pH 7.4) supplemented with is substrates (synthetic alkylamides 6, 11, 3 and 12 or the alkylamide fraction from the ethanolic liquid as required—see Figure legends for concentrations used) added from ethanolic stocks. Final ethanol concentrations were either 0.70% or 0.96% and were consistent in each assay. Reactions were initiated by the addition of an NADPH-generating system consisting of (final concentrations) 250 mM NADP+, 10 mM glucose-6-phosphate and 0.5 μ/mL glucose-6-phosphate dehydrogenase. Negative controls and cytosolic incubations lacked an NADPH-generating system. Reaction mixtures were incubated at 37° C. with gentle agitation for the duration of each experiment. Reactions were terminated by addition of an equal volume of 100% methanol to a sample aliquot. Diluted samples were then centrifuged at 16000×g for 2 minutes and supernatants stored at −20° C. until analysis by LCMS.

Incubations (0.2 mL) with recombinant enzyme preparations were performed as described above except that bacterial membrane preparations were used at 0.1 μM P450. For P450s 3A4 and 3A5, reductase concentrations were supplemented to two fold the P450 concentration by addition of membranes from cells expressing reductase alone. For P450s 2C9 and 2C19, reductase concentrations were supplemented to five fold the P450 concentration. Negative controls contained bacterial membranes derived from cells transformed with the empty expression vector alone ("pCW") or cells expressing only reductase ("hNPR"). Negative controls contained membranes added at total protein ("pCW") or reductase "hNPR") concentrations at the upper limit of those present in incubations with recombinant P450 preparations.

Analysis

Alkylamide concentrations in samples were determined by LCMS using a gradient HPLC system (Shimadzu LC10AT) coupled to a quadrupole mass spectrometer (Shimadzu, QP8000a) operating in positive SIM mode with an APCI interface. The mobile phases were a mixture of water and acetonitrile. Alkylamides 6 and 3 were detected using a 65% acetonitrile isocratic run. Alkylamides 11 and 12 were detected using an 85% acetonitrile isocratic run. The alkylamide fraction was analysed using a gradient that increased from 20% to 40% acetonitrile over the first 5 minutes, then to 80% acetonitrile over the following 15 minutes and to 100% over the next 3 minutes followed by a re-equilibration period at 20% acetonitrile prior to the next injection. A similar gradient was used in scan and then SIM (M+1 of 248, 264, 246, 192, 280 and 282) modes to identify metabolites of 3. A $C_{18}$, 3 m, 100×2.00 mm Phenomenex Luna column was used with a solvent flow rate of 0.3 mL/minute. All alkylamides were linear in the range 0.001-10 mg/mL ($R^2$>0.9) with a coefficient of variation between 4 and 5.

Results

The metabolic stability of a number of alkylamides was assessed in vitro in both the cytosolic and microsomal fractions of human livers. The ability of alkylamides to survive first pass liver metabolism was not examined. Cofactor-, enzyme- and time-dependent degradation of substrates were assessed as a measure of metabolism. No alkylamide metabolism was detected in cytosolic fractions (data not shown) and microsomal fractions exhibited no metabolism in the absence of NADPH (data not shown).

Figure 3:
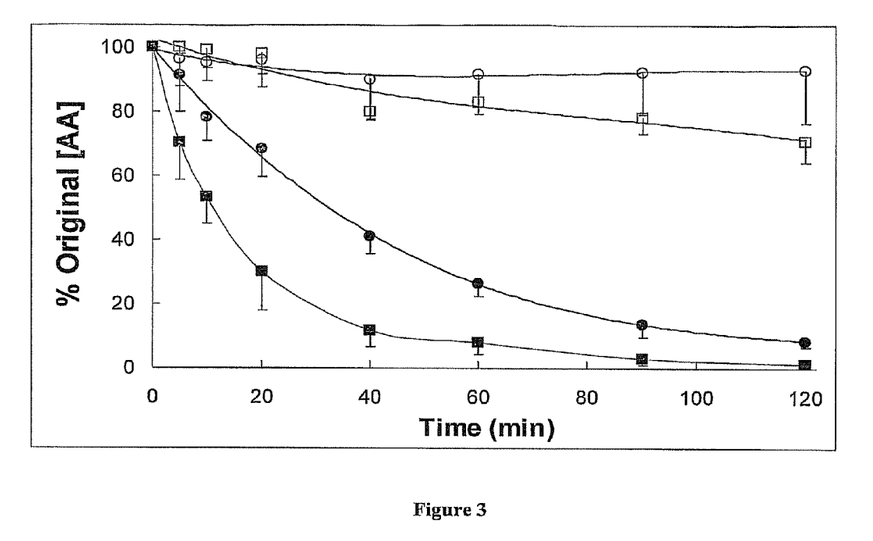
FIG. 3 shows the time-dependent metabolism of synthetic alkylamides by human liver microsomes. Incubations included (O) 43 mM (2E)-N-isobutylundeca-2-ene-8,10-diynamide 6; ( ) 20 mM (2E)-N-isobutyldodeca-2-ene-8,10-diynamide 11; (●) 40 µM (2E,4E,8Z,10Z)—N-isobutyldodeca-2,4,8,10-tetraenamide 3; or (■) 12 µM (2E,4E)-N-isobutyldodeca-2,4-dienamide 12.
Each point represents the mean±SD for 4 microsomal preparations from different livers each examined in duplicate.

A number of pure, synthetic alkylamides (6, 11 3 and 12 as shown in FIG. 1) as well as the complex mixture of alkylamides obtained from an ethanolic extract of *Echinacea* were investigated for their susceptibility to liver P450-mediated degradation in microsomal preparations from four different subjects. The concentration of each substrate remaining at the given time points was quantified with LCMS and rates of substrate depletion were calculated as a percentage of the original concentration. Substrate depletion with time was used to quantify metabolism; no alkylamide metabolites have been identified to date and hence this evaluation of substrate metabolism is a measure of metabolism through all possible pathways. From FIG. 3 it can be seen that there was a clear difference in the ability of the liver microsomal P450s to metabolise the synthetic 2-ene and the 2,4-diene alkylamides. The 2-ene alkylamides (6 and 11) were minimally metabolised over the period of the experiment. After an 120 minute incubation period with human liver microsomes, 93±16% of the original concentration of 6 and 71±7% of the original concentration of 11 remained intact. In contrast, the 2,4-dienes were rapidly metabolised with only 9±2% of the original concentration of 3 and 2±1% of the original concentration of 12 detected after 2 hours. Rates of alkylamide metabolism were two fold higher for 11, seven fold higher for 3 and ten fold higher for 12 than the rates found for 6. Little variability in alkylamide metabolism by the microsomes was observed between liver preparations (FIG. 3).

Less degradation of the 2,4-diene alkylamides was evident in the *Echinacea* preparation after incubation with the liver microsomes than seen in incubations with the corresponding pure compounds. Specifically, after incubation of an *Echinacea* alkylamide mix with human liver microsomes, 3 was still present at 66±26% of the initial levels in contrast to the 9% seen in the incubation with the synthesised pure 3. Similarly, 12 was still present at 99±14% in incubations with the *Echinacea* alkylamide mix in contrast to the 2% seen in the incubations with pure synthetic 12. In contrast to these results, 6 was essentially not metabolised in either the complex mixture (91±24% remaining after 2 hours) or in the incubation with the synthesised compound (where 93±16% remained after 2 hours).

Figure 4:
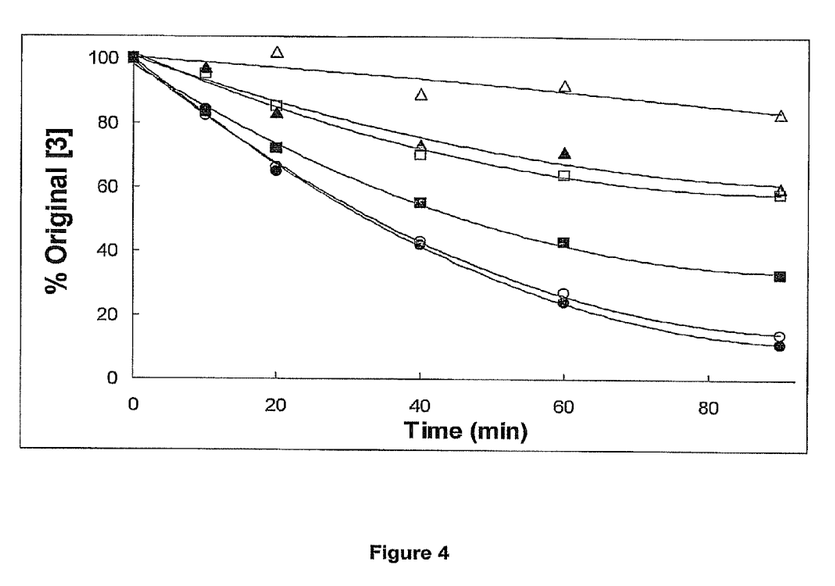
FIG. 4 shows the inhibition of synthetic (2E,4E,8Z,10Z)—N-isobutyldodeca-2,4,8,10-tetraenamide (3) metabolism by human liver microsomes in the presence of increasing concentrations of synthetic (2E)-N-isobutylundeca-2-ene-8,10-diynamide (6). Compound 3 was present at 20 µM in all experiments while 6 was present at (●) 0, (○) 0.22, (■) 2.2, ( ) 5.5, (▲) 9.0 and (Δ) 20 uM. Each point represents the mean for one microsomal preparation examined in duplicate. The deviation was less than 15 for each point. The ratio of 6 to 3 was 0, 1:91, 1:9.1, 1:3.6, 1:2.2 and 1:1 respectively.

Co-incubation of the non-metabolised 6 and the rapidly metabolised 3 at equimolar concentrations inhibited metabolism of 3 (FIG. 4) with 83±4% of the original concentration of 3 being detected in the final mixture after incubation with human liver microsomes for 90 minutes. The 2-ene 6 was found to inhibit liver P450 metabolism of the 2,4-diene 3 in a concentration dependent manner (FIG. 4). The slightly metabolised 11 did not appear to prevent metabolism of 12 (data not shown). No other combinations were examined as together, 3 and 6 comprise approximately 45% of the total alkylamides present in most ethanolic extracts where *Echinacea purpurea* and *Echinacea angustifolia* are combined. The remaining 55% is comprised of many alkylamides, none of which exceed 20% of the total, and most of which are unavailable in pure, isolated forms.

Figure 5:
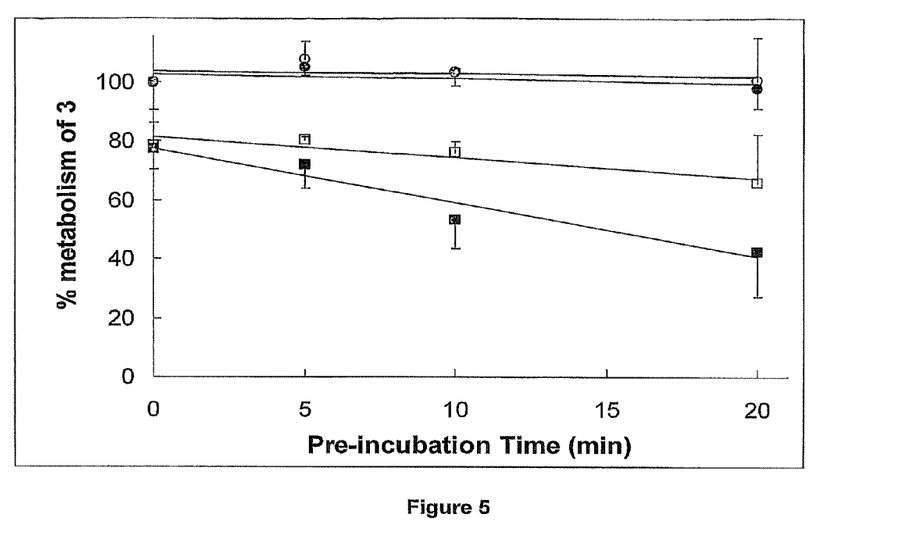
FIG. 5 shows the mechanism based inhibition of synthetic (2E,4E,8Z,10Z)—N-isobutyldodeca-2,4,8,10-tetraenamide (3) metabolism by pre-incubation with synthetic (2E)-N-isobutylundeca-2-ene-8,10-diynamide (6). All incubations included 18 µM 3 either in the presence or absence of NADPH and 4.3 µM 1 in the final incubation mix. (O)–NADPH–(1), (●)–NADPH+(1), (□)+NADPH–(1), (■)+NADPH+(1).
Each point represents the mean±SD for two different microsomal preparations examined in duplicate.

In order to investigate whether inhibition by 6 might be mechanism-based, human liver microsomes were pre-incubated in the presence or is absence of 6 and an NADPH-generating system but without 3 in the pre-incubation mix. Then, at the given time points, aliquots were removed and diluted into an incubation mix containing 3. Remaining concentrations of 3 were measured after a further 60 minute incubation period. Metabolism of 3 was significantly inhibited by pre-incubation of the microsomes with 6, in a time- and co-factor-dependent manner (FIG. 5).

A number of metabolites derived from 3 were detected by LCMS (Table 1).

TABLE 1

Chromatographic and mass spectrometric properties of metabolites of (2E,4E,8Z,10Z)-N-isobutyldodeca-2,4,8,10-tetraenamide (3).

| Retention Time (min) | Apparent MW* | Metabolite Class | Comment |
|---|---|---|---|
| 20.3 | 247 | Parent Compound (3) | |
| 13.2 | 263 | Monohydroxylation | Significant M-H2O seen in LCMS. |
| 15.8 | 263 | Monohydroxylation | Significant M-H2O seen in LCMS. |
| 16.7 | 263 | Monoepoxidation | LCMS analysis. |
| 17.4 | 263 | Monoepoxidation | LCMS comparison with synthetic standard. |
| 18.7 | 191 | N-dealkylation | LCMS analysis. |
| 23.7 | 279 | Dihydroxyl- or diepoxidation | LCMS analysis. |
| 27.4 | 281 | Monoepoxidation followed by hydrolysis | LCMS analysis. |

Single ion monitoring revealed four new peaks with an apparent molecular weight of 263 amu which would result from simple epoxidation or hydroxylation (for examples see FIGS. 52 and 2c respectively). In addition, a metabolite with MW of 191 amu was detected which would correspond to the N-dealkylated compound (FIG. 2d). Other minor metabolites were found with molecular weights of 279 (two hydroxylation/epoxidation events) and 281 amu (epoxidation followed by hydrolysis; FIG. 2e).

The epoxides corresponding to oxidation of the 8,9 (structure not shown) and 10,11 (FIG. 5b) double bonds were synthesised as a mixture via meta-chloroperbenzoic acid epoxidation of 3, and fully characterised by NMR and MS. The regiochemistry of this transformation, i.e. at the 8,9 and 10,11 alkenes rather than at the 2,3 or 4,5 alkenes, is expected. This is due to the decreased reactivity of the double bonds conjugated to the carbonyl of the amide moiety [16]. The $^1$HNMR spectrum of the epoxides confirmed this regiochemistry of oxidation. For example, the vicinal coupling constant for the hydrogens of the epoxide ring in both isomers ($^3J$=4.2-4.5 Hz) is consistent with a cis but not a trans geometry. Additionally, the shifts of the vinyl hydrogens conjugated to the amide are the same in both epoxides and the starting tetraene (3) clearly indicating that oxidation had occurred at the diene moiety adjacent to the terminal methyl. The synthetic epoxides co-eluted on the LCMS and eluted with the same retention time as seen for one of the metabolite peaks detected in the microsomal oxidation of 3 (Table 1).

A preliminary screen was performed to investigate metabolism of 3 by recombinant human P450s. Consumption of 3 was observed in incubations of P450s 1A1, 1B1, 2A13, 2C8, 2C9, 2C19, 2D6, 3A4 and 3A5 (Table 2). For all other forms, apparent substrate loss was similar to that seen in the presence of membranes from bacteria expressing no P450s.

Discussion

To the inventors knowledge, this is the first study to examine the metabolism of alkylamide components of *Echinacea*. Time- and NADPH-dependent degradation of alkylamides was observed in four different microsomal preparations suggesting these *Echinacea* components are metabolised by cytochrome P450 enzymes in human liver. A role for other microsomal enzymes including flavin-containing monooxygenases or peroxidases cannot be excluded, but the chemistry involved (NADPH-dependent oxidation at carbon centres) argues against a role for these enzymes. No significant degradation of substrates was evident in cytosolic fractions indicating little if any role for cytosolic amidases or carboxylesterases in alkylamide metabolism.

After incubation with both NADPH and human liver microsomes, 93% of the original concentration of 6 was still present after 120 minutes. In contrast, the major alkylamide found in all ethanolic extracts of *Echinacea*, (2E,4E,8Z, 10Z)—N-isobutyldodeca-2,4,8,10-tetraenamide (3), was rapidly metabolised in its pure, synthetic form but not in combination with the other alkylamides found in the ethanolic *Echinacea* extract. This suggested that metabolism of alkylamides by liver P450s was not only dependent on their structure but also on the combination of alkylamides present.

A number of potential structures would be predicted for the metabolites produced by P450-catalysed oxidation of alkylamides. For example, 3 could be oxidised at any of the four double bonds to produce the four corresponding epoxides (see FIG. 2b). Hydroxylation at any of the sp$^3$ hybridised carbons would produce the corresponding alcohols (FIG. 2c). An exception to this is hydroxylation at the CH$_2$ α to the amide nitrogen which would lead to an N-dealkylated product (FIG. 2d). The allylic epoxides (e.g. FIG. 2b) produced would also be reactive and could well undergo hydrolysis under the incubation conditions to produce diols (e.g. FIG. 2e). Finally, further transformation of the initially formed metabolites may occur leading to diepoxides, hydroxyepoxides etc.

Careful examination of the metabolites by LCMS provided evidence for all of these processes (Table 1). In particular, at least four different peaks with an apparent MW of 263 were found. This molecular weight corresponds to either hydroxylation or epoxidation of 3. One of these peaks possessed the is same retention time and mass spectral properties as the synthetic epoxide mixture examined, which clearly supports epoxidation as one of the processes involved in the metabolism of 3. Two peaks which had a MW of 263 also exhibited significant 245 (M-18 or M-H$_2$O) ions. This was not seen for the synthetic epoxides but would be expected for alcohols (e.g. FIG. 5c) produced by hydroxylation of 3.

As terminal alkynes have been demonstrated to irreversibly inactivate P450s in other instances the ability of the non-metabolised 6 to protect the rapidly metabolised 3 was investigated. Degradation of 3 was inhibited by 6 in a concentration-dependent manner. The possibility that this inhibition reflected mechanism-based inactivation of P450s due to the presence of the terminal alkyne moiety in 6 was also investigated. Mechanism-based inactivation of the P450s was supported by the finding that pre-incubation with 6 in the presence, but not the absence, of an NADPH generating system led to a decrease in 3 metabolism. The slight generalised shift towards lower metabolism in both sets of data obtained in the presence of 6 (+/− NADPH) compared to the data from 6-deficient incubations in FIG. 6 suggested an additional competitive component to the inhibition by 6.

Ethanolic preparations of *Echinacea purpurea* contain relatively low amounts of 6 compared to 3. The present inventors have analyzed such a preparation and observed that 3 represented 48% of the total alkylamides while the inhibitory 6 was present at only 1% (data not shown). Thus, it is unlikely that there would be any significant inhibition of metabolism and consequent interactions with other compounds would be expected with such a preparation. In other words, it would be expected that the bioavailability of 6 in such a preparation would be low.

These findings are unexpected and support the prospect that a 2-ene alkylamide may improve the bioavailability of 2,4-diene alkylamides due to an inhibitory activity. This is supported both by the ability of 6 to prevent P450-mediated degradation of 3 in experiments using the pure, synthetic alkylamides as well as by the inability of the human liver microsomes to catalyze significant degradation of 3 or the other 2,4-dienes in the mixed alkylamide preparation prepared from both *Echinacea angustifolia* and *Echinacea purpurea* roots (which contained 46% of 3 and 3% of 6). Increased bioavailability of 3, or any of the other alkylamides, would be important if it is responsible for the therapeutic activity of *Echinacea* preparations.

In summary, this study is the first to examine the enzyme-mediated degradation of *Echinacea* alkylamides in human liver. Evidence has been obtained for the cytochrome P450-mediated metabolism of these compounds to various epoxide, hydroxylated, and dealkylated products and for an interaction between different *Echinacea* components due to mechanism-based inactivation by the 2-ene alkylamide 6.

Clinical Studies
Subjects

Eleven healthy volunteers, males and females (age range 18-26 years; height 157-188 cm; weight 48-95 kg; BMI 19-30) consented to undertake this study. The protocol was approved by the ethics committee of the Queensland Institution of Medical Research and written informed consent was obtained in all cases. Subjects underwent a physical examination and a laboratory safety screen—routine biochemical (ELFT, beta HCG (for females)), haematological (haemoglobin, white cell count, platelet count, haematocrit, red cell count and differential white cell count) and serological (HIV, hepatitis B and hepatitis C) screening from blood and urinalysis and a full drug screen (including cannabinoids, cocaine, opioids, barbiturates and amphetamines) from urine—to ensure eligibility for participation in the study. Exclusion criteria included (i) significant intercurrent disease of any type, (ii) ingestion of *Echinacea* or related herbal substances in the four weeks prior to the study commencing, (iii) alcohol consumption greater than community norms, (iv) a history of drug habituation or any prior intravenous usage of an illicit substance, (v) detection of any illicit drug in the urine drug screen, (vi) smokers unable to refrain from smoking during the period of confinement in the study, (vii) history of allergy or intolerance to *Echinacea* or related herbs or is to plants of the daisy family, (viii) pregnancy—known or identified through the urine test- or lactation, (ix) positive tests for hepatitis b, hepatitis c or any clinically significant biochemical or haematological abnormality, (x) participation in any research involving drug administration and/or significant blood loss within the 8 weeks preceding the study and (xi) blood donation in the 8 weeks preceding the study. Subjects were not suffering from any recurrent illness and were not taking any other drugs with the exception of the contraceptive pill. Alcohol, caffeine and grapefruit juice were avoided for 24 hours prior to dosing.

Study Design

Volunteers received *Echinacea* orally (4 tablets, each containing extract equivalent to 675 mg of *Echinacea purpurea* root plus 600 mg of *Echinacea angustifolia* root prepared from the dried ethanolic extracts of the two echinacea species) at approximately 0800 hours. Tablets were taken immediately after a high-fat breakfast (1 glass of orange juice, one slice of buttered toast, one fried egg, one slice of cheese, two rashers of bacon, one serving of hash brown potatoes and one glass of whole milk—the Australianised equivalent of the FDA standard high-fat breakfast; n=9), or in the fasted state (n=2). Blood samples (10 mL) were taken prior to tablet ingestion as well as 0.33, 0.66, 1.0, 1.33, 1.66, 2.0, 2.5, 3.0, 3.5, 4, 6, 8, 10, and 12 hours post-dose, and were collected into tubes containing lithium heparin (125 I.U.). Plasma was separated by centrifugation within 0.5 hours and stored frozen (−20° C. or lower) for subsequent analysis of echinacea components. Subjects were quietly ambulant or semi-recumbent on beds for the first 4 hours after dosing.

Alkylamide Analysis

Plasma samples were thawed and re-centrifuged at 3000 rpm for 5 minutes. Supernatant (1 mL) was then mixed with 50 mM ammonium acetate (pH 8.0, 1 mL) containing internal standards (2E,4E)-N-(sec-butyl)hexa-2,4-dienamide (2,4-diene short chain standard, 699 ng/mL (FIG. 1 alkylamide 9)), (2E)-N-(sec-butyl)hex-2-enamide (2-ene short chain standard, 562 ng/mL (FIG. 1 alkylamide 10)) and 736 ng/mL chlorogenic acid (caffeic acid conjugate standard). The alkylamides were then separated from the plasma and concentrated by passage through a solid phase extraction cartridge (Phenomenex Strata C18) that was pre-rinsed with 100% methanol and conditioned with water. After sample addition, the column was washed with water (10 mL) and 25% methanol in water (5 mL) prior to alkylamide elution with 100% methanol (2 mL). The eluate was then dried under air at 37° C. and stored at 4° C. until assayed. Dried samples were reconstituted with methanol (50 mL) just prior to LCMS analysis. Recoveries of the major alkylamides, determined by spiking blank plasma with an ethanolic *Echinacea* preparation similar to that used to make the tablets ingested in this study and analysed with and without extraction, were found to be in the range 91-98% (n=3 for each). The recoveries of the compounds used as internal standards were tested in a similar manner and found to be consistent with that of the alkylamides.

LCMS Analysis

Alkylamide concentrations in samples were determined by liquid chromatography-mass spectrometry (LCMS) using a Shimadzu HPLC system coupled to a Shimadzu QP8000a single quad mass spectrometer equipped with an APCI interface operating in positive ion SIM mode (detection of M+1 ions for the individual compounds listed in FIG. 1). The mobile phase was a mixture of water and acetonitrile and was applied using a stepwise gradient. The elution gradient increased from 20% to 40% acetonitrile over the first 7 minutes, then to 80% acetonitrile over the following 13 minutes, and then to 100% acetonitrile over the next 3 minutes. A period of re-equilibration at 20% acetonitrile was then undertaken prior to the next injection. A $C_{18}$ Phenomenex Luna column (100×2.00 mm I.D. 3 μm particle size) was used with a solvent flow rate of 0.3 mL/minute. All alkylamides were linear in the range 0.001-10 mg/mL ($R^2>0.9$). Calibration curves were prepared with is each analytical batch by spiking blank human plasma with varying dilutions of an ethanolic extract similar to that used to prepare the tablets used in the study. Due to the non-availability of pure standard materials, alkylamide concentrations in the ethanolic extract were calculated as equivalents to known concentrations of the 2,4-diene and 2-ene short chain alkylamides (FIG. 1 alkylamides 9 and 10) used as internal standards. Quality control samples (also prepared from blank human plasma spiked with varying amounts of the ethanolic extract) were also prepared and processed with each batch of patient samples.

Tablet and plasma concentrations of 20 individual alkylamides were examined but only the 8 major ones have been reported in this study. The others have been summed and included in the totals for both the 2,4-dienes and the 2-enes which have then been summed to give the total alkylamide concentration.

Pharmacokinetic Analysis

The areas under the plasma concentration-time curves from 0-12 hours ($AUC_{0-12}$) for the different alkylamides were calculated using trapezoidal rule integration. Elimination half-life ($t_{1/2}$) was determined from the slope of the least squares regression line of best fit of ln-concentration vs time profiles between 4 h and 12 h post-dose. Data were combined for isomers for each alkylamide. Results are expressed as mean±SE.

Results

The chemical structure for the main alkylamides found in plasma after *Echinacea* ingestion are the compounds 1 to 8 given in FIG. 1. Table 2 to provides the phytochemical breakdown of these alkylamides in the echinacea tablets used in this study determined using LCMS in conjunction with the plasma samples. Data is expressed as Mean+/−SF (n=4).

TABLE 2

| Alkylamide | Tablet content (mg/tablet) |
|---|---|
| 2,4-dienes | |
| 1 | 0.79 ± 0.02 |
| 2 | 1.00 ± 0.03 |
| 3 | 4.29 ± 0.11 |
| 4 | 0.40 ± 0.01 |
| 5 | 0.44 ± 0.01 |
| other | 2.69 ± 0.06 |
| total 2,4-diene | 9.61 ± 0.24 |
| 2-ene | |
| 6 | 0.76 ± 0.02 |
| 7 | 0.20 ± 0.01 |
| 8 | 0.29 ± 0.01 |
| other | 0.06 ± 0.00 |
| total 2-ene | 1.31 ± 0.03 |
| total alkylamides | 10.92 ± 0.27 |

Tablet disintegration time (in water at 37° C. with a stroke depth of 50-60 mm and a stroke rate of 28-32 per min) in a standard disintegration apparatus was 13 minutes. Compartmentation of alkylamides was examined in blank blood spiked with an alkylamide mix; the alkylamides were found to remain in the plasma and not to partition into blood cells (data not shown).

Figure 6:
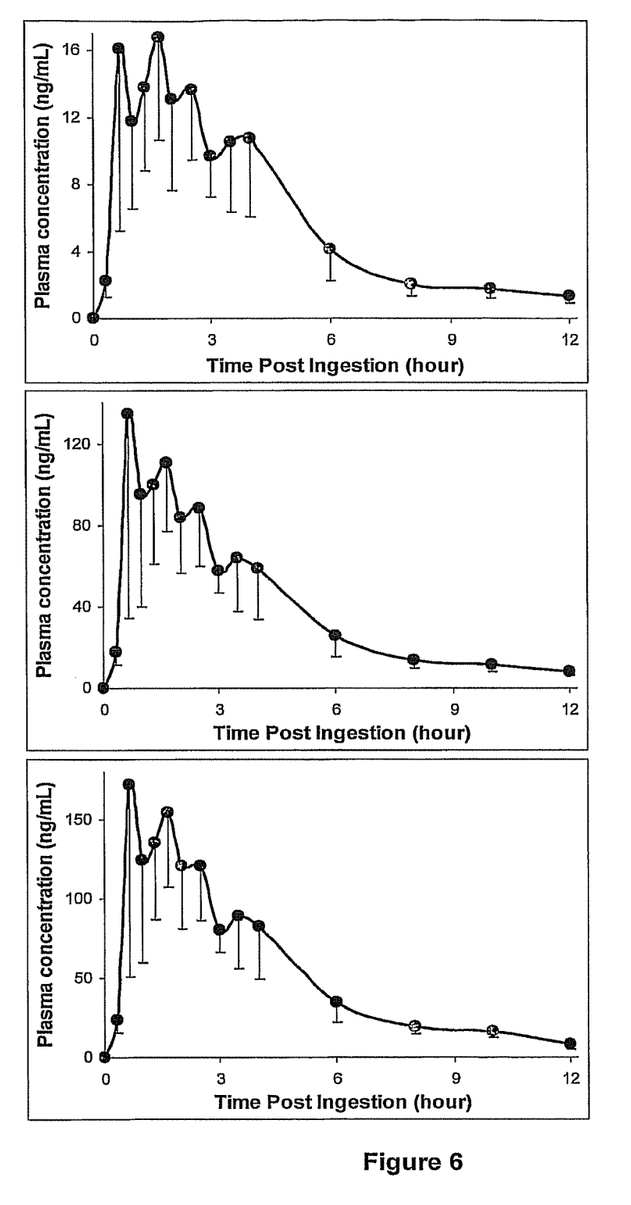
FIG. 6 shows plasma 2,4-diene alkylamide concentration time curves for fed subjects. (a) (2E,4Z,10Z)—N-isobutyldodeca-2,3,10-triene-8-ynamide (2); (b) (2E,4E,8Z,10Z)—N-isobutyldodeca-2,4,8,10-tetraenamide (3); (c) total 2,4-dienes. Values are Means±SE for 9 subjects.
Figure 7:
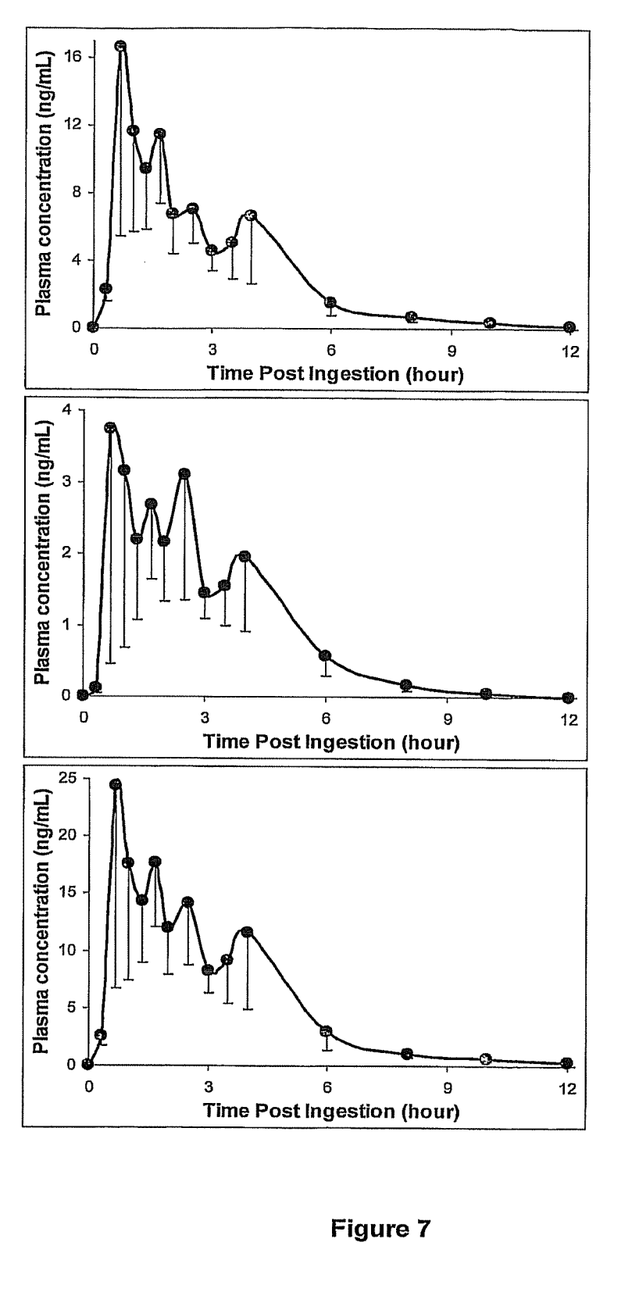
FIG. 7 shows Plasma 2-ene alkylamide concentration time curves for fed subjects. (a) (2E)-N-isobutylundeca-2-ene-8,10-diynamide (6); (b) (2E,9Z)—N-isobutylpentadeca-2,9-diene-12,14-diynamide (8); (c) total 2-enes. Values are Means±SE for 9 subjects.

The bioavailabilities of *Echinacea* components were examined by to investigating plasma concentrations after oral dosing with an *Echinacea* preparation ingested following a standard high fat breakfast. Alkylamides were found to be rapidly absorbed and were detected in plasma at the first sampling point (20 minutes post dosing). Plasma concentration-time profiles of the 2,4-diene and 2-ene alkylamides after oral administration of the *Echinacea* preparation are shown in FIGS. 6 and 7 respectively. Although approximately 130 mg of caffeic acid conjugates were ingested by the volunteers, they were not detected in any of the plasma samples.

The representative time course for the sum of all alkylamides present in human plasma is shown in FIG. 6a. One subject had significantly higher plasma concentrations and faster absorption rates for all alkylamides. When total alkylamide concentrations for all 9 individuals were averaged as in FIG. 6a, an apparent $T_{max}$ of 40 minutes is seen which is greatly influenced by this fast absorbing subject 9. Despite this pronounced effect on the apparent $T_{max}$ in the concentration time curves by this one subject, removal of this subject's data did not significantly alter the calculated values. $C_{max}$ decreased from 336±131 to 215±58 ng equiv/mL, $T_{max}$ increased from 2.3±0.5 to 2.5±0.5 hours and $AUC_{0-12}$ decreased from 714±181 to 591±150 mg equiv.hr/L (Mean±SE for n=9 and n=8 subjects respectively).

The effect of the absence of food on alkylamide oral availability was examined in two subjects who ingested echinacea tablets following an overnight fast. No differences were observed for the disposition of individual or total alkylamides in the fasted versus the fed subjects.

Discussion

The present study investigated the disposition and pharmacokinetics of phytochemicals from a dry ethanolic preparation of *Echinacea* ingested in tablet form. Alkylamides were detected in plasma at the first sampling time (20 minutes after dosing) from both fed and fasted subjects and remained at measurable concentrations for the 12 hours of the study.

Bioavailability is essentially defined as the fraction of a given dose of compound that reaches the systemic circulation as intact compound. As is the case for prescription pharmaceuticals, it is necessary to know the amounts of the potentially active constituents (in this case the various alkylamides) present in the *Echinacea* products ingested. Many previous clinical trials is investigating the efficacy of *Echinacea* preparations have not disclosed these phytochemical profiles making direct comparison of one study to another impossible. The phytochemical profile of any herb is dependent on many factors including growing conditions and post-harvest treatment Differences in either or both of these can contribute to marked differences in the phytochemical profiles of different batches from the same manufacturer, let alone from different sources. The alkylamide content of the tablets given in Table 2 are therefore only relevant for the particular batch of *Echinacea* used in this study.

It may therefore be appreciated that for therapeutic use it is important to provide an *Echinacea* formulation having a level of 2-ene sufficient to inhibit metabolism of the 2,4-enes present and/or to standardize formulations according to 2-ene content.

The fast appearance of alkylamides in plasma (20 minutes) is in agreement with the ease of uptake seen with their rapid permeation across Caco-2 monolayers [1]. It is also in agreement with the tablet disintegration time of 13 minutes. The presence of food appears to make no difference to the speed of alkylamide uptake into the plasma as plasma concentrations in the fasted state were within the range found for subjects who ingested *Echinacea* after a standard high fat breakfast. The alkylamides exhibit classic single dose pharmacokinetic profiles, both individually and as a summed total group. Maximum plasma concentrations for the individual alkylamides differ as expected based on the varying amounts of each present in the starting material.

Thus it may be seen that protecting the akylamide fraction from liver metabolism may enhance the bioavailability of solid *Echinacea* formulations in particular.

It may therefore be appreciated that for therapeutic use it is important to provide an *Echinacea* formulation having a level of 2-ene sufficient to inhibit metabolism of the 2,4-enes present and/or to standardize formulations according to 2-ene content.

In the specification the term "comprising" shall be understood to have a broad meaning similar to the term "including" and will be understood to imply is the inclusion of a stated integer or step or group of integers or steps but not the exclusion of any other integer or step or group of integers or steps. This definition also applies to variations on the term "comprising" such as "comprise" and "comprises".

It will be appreciated that various changes and modifications may be made to the invention as described herein without departing from the spirit and scope thereof.

REFERENCES

1. Matthias A.; Blanchfield J. T.; Penman K. G.; Toth I.; Lang C-S.; De Voss J. J.; Lehmann R. P. Permeability studies of alkylamides and caffeic acid conjugates from echinacea using a Caco-2 cell monolayer model. *J. Clin. Pharm. Therap.* 2004, 29: 7-13.
2. F. P. Guengerich, Analysis and characterization of enzymes. In: Principles and Methods of Toxicology 3$^{rd}$ edition (Hayes, A. W., Ed.); (1994) pp 1259-1313, Raven Press, Ltd., New York.
3. T. H. Richardson, F. Jung, K. J. Griffin, M. Wester, J. L. Raucy, B. Kemper, L. M. Bornheim, C. Hassett, C. J. Omiecinski, E. F. Johnson, A universal approach to the expression of human and rabbit cytochrome P450s of the 2C subfamily in *Escherichia coli*, Arch. Biochem. Biophys. 323 (1995) 87-96.
4. A. Parikh, E. M. J. Gillam, F. P. Guengerich, Drug metabolism by *Escherichia coli* expressing human cytochromes P450, Nat. Biotech. 15 (1997) 784-788.
5. L. M. Notley, C. J. F. de Wolf, R. M. Wunsch, R. G. Lancaster, E. M. J. Gillam, Bioactivation of tamoxifen by recombinant human cytochrome P450 enzymes, Chem. Res. Toxicol. 15 (2002) 614-622.
6. E. M. J. Gillam, T. Baba, B.-R. Kim, S. Ohmori, F. P. Guengerich, Expression of modified human cytochrome P450 3A4 in *Escherichia coli* and purification and reconstitution of the enzyme, Arch. Biochem. Biophys. 305 (1993) 123-131.
7. T. Omura, R. Sato, The carbon monoxide-binding pigment of liver microsomes. I. Evidence for its hemoprotein nature, J. Biol. Chem. 239 (1964) 2370-2378.
8. Y. Yasukochi, B. S. S. Masters, Some properties of a detergent-solubilised NADPH-cytochrome c (cytochrome P450) reductase purified by biospecific affinity cromatography, J. Biol. Chem. 251 (1976) 5337-5344.

The invention claimed is:

1. A method of increasing the therapeutic activity of an *Echinacea* formulation comprising the steps of: providing an extract of *Echinacea angustifolia* and an extract of *Echinacea purpurea*, and combining the extracts in amounts sufficient to result in a formulation having a weight ratio of 2-ene alkylamide to 2,4-diene alkylamide of between about 1:15 and about 2:1, and wherein the bioavailability of the 2,4-diene alkylamide is improved.

2. A method of increasing the therapeutic activity of an *Echinacea* formulation that includes a combination of *Echinacea angustifolia* and *Echinacea purpurea*, the method including the steps of:
 (i) determining the 2-ene alkylamide and 2,4-diene alkylamide content of an extract of *Echinacea angustifolia*;
 (ii) determining the 2,4-diene alkylamide content of an extract of *Echinacea purpurea*; and
 (iii) combining the extract of *Echinacea angustifolia* and the extract of *Echinacea purpurea* such that the weight ratio of 2-ene alkylamide to 2,4-diene alkylamide in the combination is between about 1:15 and about 2:1;
 wherein the bioavailability of the 2,4-diene alkylamide is improved.

3. The method according to claim 1 wherein the weight ratio of the 2-ene alkylamide to the 2,4-diene alkylamide fraction of said *Echinacea* formulation is between about 1:10 to about 1:2.

4. The method according to claim 1 wherein the 2-ene alkylamide fraction includes (2E)-N-isobutylundeca-2-ene-8,10-diynamide.

5. The method according to claim 1 wherein the 2-ene alkylamide fraction includes at least about 30 wt % (2E)-N-isobutylundeca-2-ene-8,10-diynamide.

6. The method according to claim 1 wherein the extract of *Echinacea angustifolia* is at least partially sourced from *E. angustifolia* root.

7. The method according to claim 1 wherein the 2,4-diene alkylamide fraction includes (2E,4E,8Z,10Z)—N-isobutyldodeca-2,4,8,10-tetraenamide.

8. The method according to claim 1 wherein the 2,4-diene alkylamide fraction includes at least about 30 wt % (2E,4E,8Z,10Z)—N-isobutyldodeca-2,4,8,10-tetraenamide.

9. The method according to claim 1 wherein the 2-ene alkylamide fraction includes (2E)-N-isobutylundeca-2-ene-8,10-diynamide and the 2,4-diene alkylamide fraction includes (2E,4E,8Z,10Z)—N-isobutyldodeca-2,4,8,10-tetraenamide, and the *Echinacea* formulation produced has a weight ratio of 2-ene alkylamide fraction:2,4-diene alkylamide fraction of between about 1:10 to about 1:1.9.

10. The method of claim 9 wherein the weight ratio is between about 1:6 to about 1:2.

11. The method according to claim 1 wherein said *Echinacea* formulation is a solid unit dosage form.

12. The method according to claim 1 wherein said *Echinacea* formulation is in a liquid form.

* * * * *

UNITED STATES PATENT AND TRADEMARK OFFICE
CERTIFICATE OF CORRECTION

PATENT NO. : 9,205,121 B2  
APPLICATION NO. : 12/882723  
DATED : December 8, 2015  
INVENTOR(S) : Reg Lehmann et al.

Page 1 of 1

It is certified that error appears in the above-identified patent and that said Letters Patent is hereby corrected as shown below:

IN THE SPECIFICATION

1. At column 1, line number 57, the word "*paffida*" should read "*pallida*";

2. At column 2, line number 38, the third word in the line "is" should be deleted;

3. At column 3, line number 65, the third word in the line "is" should be deleted;

4. At column 6, line number 28, the third word in the line "is" should be deleted;

5. At column 7, line number 33, the "()" should read "(□)";

6. At column 7, between line 44 and 45, the "()" should read "(□)";

7. At column 8, line number 57, the second word in the line "is" should be deleted;

8. At column 9, line number 23, the third word "ILL" should read "IL";

9. At column 9, line number 29, the fourth word "is" should be deleted;

10. At column 12, line number 53, the last word "is" should be deleted; and

11. At column 13, line number 63, the ninth word "is" should be deleted.

Signed and Sealed this  
Twenty-sixth Day of April, 2016

Michelle K. Lee  
*Director of the United States Patent and Trademark Office*